(12) United States Patent
Dybe et al.

(10) Patent No.: US 10,500,300 B2
(45) Date of Patent: Dec. 10, 2019

(54) MULTI-LAYER WOUND CARE PRODUCT WITH PERFORATED RELEASE LAYER

(71) Applicant: BSN Medical GmbH, Hamburg (DE)

(72) Inventors: Verena Dybe, Hamburg (DE); Sascha Casu, Hamburg (DE)

(73) Assignee: BSN Medical GmbH, Hamburg (DE)

( * ) Notice: Subject to any disclaimer, the term of this patent is extended or adjusted under 35 U.S.C. 154(b) by 0 days.

(21) Appl. No.: 16/471,066

(22) PCT Filed: Dec. 19, 2017

(86) PCT No.: PCT/EP2017/083418
§ 371 (c)(1),
(2) Date: Jun. 19, 2019

(87) PCT Pub. No.: WO2018/114871
PCT Pub. Date: Jun. 28, 2018

(65) Prior Publication Data
US 2019/0328926 A1    Oct. 31, 2019

(30) Foreign Application Priority Data

Dec. 20, 2016 (EP) .................................. 16205251

(51) Int. Cl.
| | | |
|---|---|---|
| *A61L 15/44* | (2006.01) | |
| *A61L 15/42* | (2006.01) | |
| *A61L 15/60* | (2006.01) | |
| *A61K 9/70* | (2006.01) | |

(52) U.S. Cl.
CPC ............ *A61L 15/44* (2013.01); *A61L 15/425* (2013.01); *A61K 9/7092* (2013.01); *A61L 15/60* (2013.01); *A61L 2300/114* (2013.01)

(58) Field of Classification Search
CPC ............... A61L 15/42–44; A61L 15/60; A61L 2300/114; A61K 9/7023–7092
See application file for complete search history.

(56) References Cited

FOREIGN PATENT DOCUMENTS

| WO | 2012052561 A2 | 4/2012 | |
|---|---|---|---|
| WO | WO-2016032833 A1 * | 3/2016 | ............. A61L 15/38 |
| WO | 2016079538 A1 | 5/2016 | |
| WO | WO-2016079538 A1 * | 5/2016 | ........... A61K 9/0014 |

OTHER PUBLICATIONS

International Searching Authority, Search Report issued in International Application No. PCT/EP2017/083418 dated Mar. 1, 2018 (2 pages).
International Searching Authority, Written Opinion of the International Preliminary Examining Authority issued in International Application No. PCT/EP2017/083418 dated Nov. 15, 2018 (7 pages).
International Searching Authority, Notification of Transmittal of the International Preliminary Report on Patentability issued in International Application No. PCT/EP2017/083418 dated Mar. 6, 2019 (7 pages).

* cited by examiner

*Primary Examiner* — H. Sarah Park
(74) *Attorney, Agent, or Firm* — Wood Herron & Evans LLP

(57) ABSTRACT

A multi-layered wound care product includes an upper liquid-absorbing layer, an intermediate occlusive layer; and an active agent-releasing bottom layer. The latter two layers have common pores or perforations that enable the passage of wound exudate through the two layers to reach the liquid-absorbing layer. A use of the multi-layered wound care product for treatment of acute and chronic wounds and a method of producing the multi-layered wound care product are also provided.

19 Claims, 5 Drawing Sheets

MULTI-LAYER WOUND CARE PRODUCT WITH PERFORATED RELEASE LAYER

CROSS-REFERENCE TO RELATED APPLICATION

This application is a national phase application of, and claims priority to, International Application No. PCT/EP2017/083418, filed Dec. 19, 2017, which claims the benefit of European Patent Application Serial No. 16205251.8, filed Dec. 20, 2016, the disclosures of which are incorporated by reference herein in their entireties.

FIELD OF THE INVENTION

The invention relates to a multilayered wound care product comprising an upper liquid-absorbing layer, an intermediate occlusive layer; and an active agent-releasing bottom layer the latter two having common pores or perforations allowing the passage of wound exudate. The invention further relates to the use of said wound care product for treatment of acute and chronic wounds. The invention finally relates to a method of producing the wound care product.

BACKGROUND OF THE INVENTION

The molecular and cellular mechanisms underlying the repair of the skin tissue has not been sufficiently investigated yet. As a consequence, the failure of the skin tissue to heal is still poorly understood, and current therapies are quite limited. Improper wound healing after trauma, acute illness, surgical interventions, or chronic disease conditions affects millions of people worldwide each year and is the consequence of misregulated elements of the tissue repair program that occurs in healthy tissue response. The repair response is a complex process which includes inflammation, angiogenesis, deposition of extracellular matrix and cell recruitment. Notably, the failure of one or more of the above stated cellular processes is generally linked to an underlying clinical condition, such as vascular disease, diabetes or aging, which are all frequently associated with healing pathologies (Eming et al., 2014; Science Translational Medicine, (6), 265: 1-15).

The process of wound healing is a dynamic one, and involves complex and phase-dependent interactions between cells, extracellular matrix (ECM), ECM components such as growth factors that work together to reconstitute tissue following injury (Clark et al., 2007, 127(5): 1018-1029). The wound healing processes can be classified into the following four phases: the inflammatory or exudative phase (cleansing phase), the granulation phase, the epithelization phase, and the reparative phase. The epithelization phase and the reparative phase are occasionally considered as one. The challenge of a successful wound care treatment is to specifically address the different requirements of the above described healing phases.

Within wound care management the wound infection, the protease imbalance and the exudate management proved to be three key aspects which have to be addressed for promoting the wound healing.

Exudate Management

The generation of wound exudate occurs as a consequence of vasodilation that takes place during the early inflammatory phase of the wound healing as induced by inflammatory transmitters such as bradykinin and histamine. The wound exudate is a serous fluid contained within the wound bed and represents a part of normal wound healing process in acute wounds. However, as soon as the wound becomes a chronic non-healing wound with abnormal, persistent inflammation or with an established infection, the exudate plays a different role and will become a challenge in the wound care treatment. Notably, the wound exudate as generated in chronic wound contains components which are not observed in exudate from acute wounds such as proteolytic enzymes and other deleterious components. Hence, the chronic wound exudate has been regarded as 'a wounding agent in its own right' because it induces the degradation of growth factors and peri-wound skin tissue and makes the tissue vulnerable to further inflammation.

As a consequence of the above mentioned effects of wound exudate, an effective exudate management has now become a key strategy within the treatment of chronic exuding wounds. First products show that the exudate management allows to accelerate the healing process, reduces the exudate-related problems such as infection and maceration, reduces frequency for changing the wound dressings and ultimately improves healthcare efficiency in view of costs and increases quality of life for the patient.

Wound dressings represent the dominant option for managing the wound exudate within the wound site. An optimal dressing should combine two different, in some respect contradictory effects: The dressings should remove excessive wound exudate but in the same instance retain a certain wound moisture. Most of the dressing materials remove the wound exudate by absorption within the dressing or by allowing an exudate evaporation. The simplest absorptive materials exhibit void spaces within their structure for taking up the fluids. Examples are viscose cotton, or polyester fabrics and polymer foams e.g. made from silicone or polyurethane. Notably these "simple" absorbers are not able to retain the wound exudate under pressure. In contrast there are improved dressing materials, such as hydrocolloids, alginates, carboxymethylcellulose (CMC) fibers and especially superabsorbent polymers (SAP) which have the ability to absorb higher amounts of liquids and furthermore, by forming a hydrogel, to retain a high proportion of said absorbed exudate even under pressure. Notably, for strongly exuding wounds the combination of absorbing wounds dressing together with negative pressure has been observed to be beneficial.

Imbalance of Healing Promoting Factors

The chronification is caused by or associated with an imbalance of factors that enable a proper wound healing. For example an excess of matrix metalloproteases such as collagenase or gelatinase A or B degrade matrix components, such as fibronectin, as well as various key growth factors, all of which are required for cell growth and the remodelling of the extracellular matrix. Furthermore, it was found out that the addition of certain growth factors, chemokines or cytokines can accelerate the wound healing process such as epidermal growth factor (EGF), transforming growth factor-beta (TGF-β), or platelet-derived growth factor (PDGF).

NO as Multi-Effective Key Player

Furthermore the gas nitric oxide was found out to represent a key role in wound healing having several modes of actions such as antimicrobial properties, modulation of cytokine function, modulation of platelet function, vasodilatory effects, promotion of angiogenesis and matrix deposition. While first results of administering nitric oxide to skin wounds have shown substantial promise, the current modalities suffer from varying drawbacks, such as administration site irritation due to NO overdosing or the burden of large, expensive equipment.

Although there are wound care articles in the prior art which addresses some of the above discussed key aspects there is still no dressing that represents a proper combination of the different aspects such as wound exudate management and undisturbed release of bioactive agents, especially NO.

Hence, there is still a need for an improved wound care product that addresses the different complex requirements for an improved wound healing. The objective of the present invention thus is to provide a wound care product which overcomes at least one of the above mentioned disadvantages.

This problem is solved by provision of a wound care product Specific embodiments are described below.

SUMMARY OF THE INVENTION

In a first aspect the present invention provides a multi-layered wound care product comprising:
(a) an upper liquid-absorbing layer;
(b) an intermediate occlusive layer; and
(c) an active agent-releasing bottom layer;
wherein the occlusive layer and the active agent-releasing layer are sheet-like layers with common pores or perforations that enable the passage of wound exudate through said two layers to reach the liquid-absorbing layer.

The wound care product of the present invention has several advantages over wound care products known in the prior art.

The multi-layer structure considers the complexity of wound pathophysiology and the different requirements during the wound-healing process. Hereby, the different layers address the following key problems:

The bottom active agent releasing layer releases bioactive, healing-promoting substances that enter the wound site.

The upper liquid absorbing layer removes excessive exudate and provides a moist wound healing.

The intermediate occlusive layer prevents the active agent from spreading to the liquid—absorbing layer.

Furthermore the pores or perforations that are provided in the sublayer-structure comprising the occlusive layer and the active agent-releasing layer enable the passage of wound exudate through said two layers to reach the liquid-absorbing layer.

Simultaneously, the active agent can be released from the area between the pores or perforations and can enter the wound site.

As a consequence of this spatial separation the wound care article combines two substance flows in the opposite direction which do not interfere with each other. Thereby the beneficial effects of the wound exudate management and the active agent release work together in a synergistic manner to yield an optimized wound treatment.

As the inventors found out, this specific layer structure with the layering sequence has the potential for improved wound healing.

At first the top liquid-absorbing layer promotes a liquid stream from the wound through the bottom and intermediate layer. Thereby the proteases and the bacteria are co-eluted with the exudate and can be also absorbed in the liquid-absorbing layer.

Although there is a general exudate flow from the wound to the absorbing layer, it still allows the release of active agents from the bottom active agent-releasing layer to the wound site.

Notably, the multi-layer structure of the present invention can be provided with additional layers such as, e.g., a covering layer.

By an individual selection of the bottom, intermediate and top layer the wound care product can easily be adapted to the specific requirements of the underlying injury. Hence, it offers an enormous flexibility of application while addressing the different phases of wound healing.

Since the wound care product of the invention is based on known components, it can be easily produced in a cost efficient manner.

DETAILED DESCRIPTION OF THE INVENTION

The inventive wound care product may be used as such, as a dressing or in combination with a backing known in the art. For example, the wound care product according to the present invention may be temporarily adhered to a backing. This backing may be removed from the wound care product once applied to the wound.

Liquid-Absorbing Layer

According to the invention, the wound care article comprises a liquid-absorbing layer. The liquid absorbing layer absorbs the liquid released by the wound which is mainly the wound exudate. As the most proximal layer with regard to the two other layers of the invention it triggers a flow of the wound exudate through the pores or perforations of the two other layers with the result that the wound exudate will not interfere with the release of the active agent. By absorbing the deleterious wound exudate and meanwhile providing a moist wound climate this layer promotes the process of wound healing.

The liquid absorbing layer of the wound care article can be made from various medically safe materials, such as open-cell foam plastic, gel or textile.

In one embodiment of the invention the liquid-absorbing layer comprises, consists essentially of, or consists of at least one absorbent material selected from the group consisting of polymer foams, sponges, hydrocolloids, hydrogels and hydrophilic polymers such as superabsorbing polymers.

Preferably, it consists of at least one layer of a hydroactive fiber or another textile material comprising hydroactive polymers such as superabsorbent polymers.

Hydroactive polymers can be selected from the list consisting of superabsorbent polymers, alginates, hydrogel nanoparticles and combinations thereof.

The term "hydroactive polymers" is to be understood hereinafter as referring to polymers capable of binding large amounts of liquid. Said polymers preferably comprise superabsorbent substances comprising polyacrylates, modified cellulose and/or alginates.

In one embodiment of the invention, the protein collagen is not included in the liquid absorbing layer.

In a preferred embodiment of the invention the upper liquid-absorbing layer further comprises at least one antimicrobial active compound, preferably selected from the group consisting of bacteriocin like inhibitory substance (BLIS), silver based compound, biguanide salt like polyhexamethylbiguanide (PHMB), chlorhexidine, phenol derivatives, such as thymol and eugenol, chlorophenol and chlordiphenyl ether.

Liquid uptake capacity and liquid retention refer to the ability of an absorbent material to take up liquids and bind/retain them, respectively. It is generally expressed in grams of a liquid (for example distilled water or 0.9% saline) per gram of absorbent material. Both parameters are a function of the properties of the hydroactive polymer, of its proportion in relation to the overall product and also of the chemical and physical makeup of the overall product.

Superabsorbent polymers (SAPs) are manufactured polymers capable of imbibing liquids to a multiple—up to 1000 times—of their own weight. Chemically, they comprise a copolymer of acrylic acid (propenoic acid, $C_3H_4O_2$) and sodium acrylate (sodium salt of acrylic acid, $NaC_3H_3O_2$), wherein the ratio between the two monomers may vary. A so-called core-crosslinker (CXL) is additionally included in the monomer solution to join the resultant long-chain polymeric molecules together in places by means of a network of chemical bridges (known as "crosslinks"). These bridges render the polymer insoluble in water. On ingress of water or aqueous salt solutions, the polymer bead swells up and causes this network of crosslinks to tauten at a molecular level, so the water is no longer able to escape unaided. The superabsorbent polymers may be present in the wound care article of the present invention in the form of a granular material, in the form of a powder, in the form of a loose aggregation, in the form of a compacted aggregation, in the form of a foam, in the form of fibers, in the form of a fibrous knit, laid or nonwoven web fabric and/or a fibrous wadding.

Alternatively, the chosen superabsorbents may be methylacrylic acid based, polyvinyl alcohol-maleic anhydride copolymers, polysaccharide-maleic anhydride copolymers, maleic acid derivatives, acrylamidopropanesulfonic acid copolymers, starch-acrylonitrile graft polymers, gelatinized starch derivatives, alkyl- or hydroxyalkylcellulose, carboxymethylcellulose, starch-acrylic acid graft polymers, vinyl acetate-acrylic ester copolymers, acrylonitrile copolymers or acrylamide copolymers.

Modified cellulose preferably comprises derivatives of cellulose, preferably sulfoalkylated cellulose and derivatives thereof, preferably cellulose ethyl sulfonates, carboxy alkylated cellulose, preferably carboxymethylcellulose, carboxyethylcellulose and/or carboxypropylcellulose, more complex cellulose derivatives, such as sulfoethylcarboxymethylcellulose, carboxymethylhydroxyethylcellulose, hydroxypropyl-methylcellulose, and amidated cellulose derivatives, such as carboxymethylcellulose amide or carboxypropylcellulose amide. Carboxymethylcellulose takes the particular form of sodium carboxymethylcellulose and is commercially available under the name of "Hydrofaser". In hygiene and wound products, the fibers are converted into a planar matrix. As they take up liquid from the wound exudate, the fibers are gradually transformed into a gel pad wherein the liquid is held and not reemitted. The construction of the fibers in question is such that the wound exudate is only taken up in the vertical direction. As a result, the exudate will not flow over the wound edge as long as there is sufficient capacity. This is an effective way to prevent wound edge maceration.

Said hydroactive polymers may also comprise alginates. Alginates are obtained from brown algae and processed into a fibrous nonwoven web. Chemically, alginates are polysaccharides, specifically calcium and/or sodium salts of alginic acids. Alginates are capable of absorbing up to 20 times their own weight of liquid, the wound exudate being imported into the void spaces. The $Ca^{2+}$ ions in the alginate lattice are exchanged for the $Na^+$ ions from the exudate until the alginate has reached its point of saturation with sodium ions. In the process, the wound dressing swells up and the alginate fiber is transformed into a gel body as a result of the fibers swelling up.

Said hydroactive polymers may similarly also comprise hydrogel nanoparticles comprising hydroxy-terminated methacrylate monomers, such as 2-hydroxyethyl methacrylate (HEMA) and/or 2-hydroxypropyl methacrylate (HPMA), which are marketed as Altrazeal, for example.

It is particularly preferable for at least one wound care article of the set to further comprise a fibrous nonwoven web comprising cellulose fibers which hereinafter are also referred to as an absorbent body.

The absorbent body may preferably comprise an essentially flat absorbent body which is made of an absorbent material and which consists of an imbibing fibrous nonwoven web incorporating superabsorbent polymers dispersed therein. These may be present in the form of a granular material, in the form of a powder, in the form of a loose aggregation, in the form of a compacted aggregation, in the form of an foam, in the form of fibers, in the form of a fibrous knit, laid or nonwoven web fabric and/or a fibrous wadding.

The absorbent body in question comprises at least one material selected from the group containing a mat, in particular fibrous nonwoven web airlaid from said yarns or fibers of superabsorbent polymers having incorporated superabsorbent polymers, and/or a loose filling of superabsorbent polymers. Said airlaid mat may preferably include an essentially flat portion of absorbent material, said portion of absorbent material consisting for example of an imbibing fibrous nonwoven web formed from the fibers mentioned and having superabsorbent polymers dispersed therein.

This absorbent body may correspond to the absorbent insert that is present in an assignee wound dressing as for example disclosed in WO 2003/094813 A1, WO 2007/051599 A1 and WO 2000/152780 A1 and is marketed under the trade name "Sorbion sachet". The disclosure of the cited documents is hereby fully incorporated in the disclosure of this document by reference.

The absorbent body in some other configuration may similarly form a core which comprises optionally flock like-fibers or yarns of superabsorbent polymers and also superabsorbent polymers in granule form, in which case the granules are adhered and/or fused to the fibers/yarns at two or more heights, and the granules are distributed across more than 50% of the entire design height of a portion of the core at least, in which case there are mingled regions of granules and fibers. The weight fraction of superabsorbent polymers here may preferably be in the range between 10 to 25 wt.-%. Similar designs are known from conventional incontinence materials and like sanitary napkins are known for their cushioning properties. A cover may be disposed around said core in an overlapping arrangement in regions, and which for example conceals an adhered seam and/or is part thereof.

It is particularly preferable for the absorbent body to comprise a fibrous web, preferably a nonwoven or Airlaid web which consists of superabsorbent fibers ("SAPs", preferably polyacrylates) or contains same as a constituent part. The fibers may for example be blended with fluff pulp (cellulose) or with polyester fibers. A layered construction may be provided as an alternative or in addition.

The absorbent body in some other configuration may similarly contain at least one flat ply comprising superabsorbent polymer fibers or yarns having superabsorbent polymers adhered in granule form. This, in a preferred configuration, results in a construction for the body where there are at least two layers in that at least one top layer puts a layer comprising superabsorbent polymers underneath. A second, flanking top layer may optionally be provided.

In one embodiment the fibers and superabsorbent polymers in the plane are merely fixed by adjacencies between the two materials. The optionally provided plurality of plies may in one preferred configuration also be physically compacted together by rolling, pressing, calendering or similar processes.

One example of polyacrylate fibres is SAF™, commercially available fibres sold by Technical Absorbent Limited (Grimsby, UK). SAF™ is formed from a cross-linked polymer of acrylic acid (AA) methylacrylate (MA) and a small quantity of special acrylate/methylacrylate monomer (SAMM) in which the acrylic acid is partially neutralised to the sodium salt of acrylic acid (AANa). SAF™ fibres are available in different staple lengths, linear density and with different degrees of cross linking to give different absorbency levels. Thus, in some embodiments the superabsorbent gel-forming fibre is SAF.

It is particularly preferable for said absorbent layer to have an area dimension of 5×10, ×20, 10×20, 10×10, 10×15 or 15×15 cm.

The basis weight in this case may be in the range between ≥50 and ≤2000 g/m². Preference is here given to basis weights of 50, 100, 150, 200, 250, 300, 350, 400, 450, 500, 550, 600, 650, 700, 750, 800, 850, 900, 950, 1000, 1050, 1100, 1150, 1200, 1250, 1300, 1350, 1400, 1450, 1500, 1550, 1600, 1650, 1700, 1750, 1800, 1850, 1900, 1950, and/or 2000 each ±25 g/m².

Thickness may here be in the range between ≥2 and ≤50 mm. Preference is given to thicknesses of 2, 3, 4, 5, 6, 7, 8, 9, 10, 12, 14, 16, 18, 20, 22, 24, 25, 26, 28, 30, 32, 34, 36, 38, 40, 42, 44, 46, 48, or 50 each ±1 mm.

Liquid retention, measured with distilled water can be between ≥5 and ≤100 g/g. Preference in this case is given to values of 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99 and/or 100 g/g.

The uptake capacity may here be in the range between ≥3 and ≤30 ml of 0.9% saline/m² at 0.2 psi pressure. Preference here is given to values of 3, 4, 5, 6, 7, 8, 9, 10, 11, 12, 13, 14, 15, 16, 17, 18, 19, 20, 21, 22, 23, 24, 25, 26, 27, 28, 29, and/or 30 ml of 0.9% saline/m². Alternatively, the uptake capacity can be in the range between ≥2 and ≤50 g of water/g. Preference in this case is given to values of 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, and/or 50 g of water/g.

The overall content of superabsorbent polymers may here be in the range between ≥5 and ≤100% w/w. Preference is here given to values of 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99 and/or 100% w/w.

Tensile strength may here be in the range between ≥5 and ≤80 N/5 cm. Preference is here given to values of 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79 and/or 80 N/5 cm.

Extensibility here can be in the range between ≥10 and ≤80%. Preference is here given to values of 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79 and/or 80%.

When superabsorbent fibers are used, the following types have turned out to be particularly advantageous in practice, as shown in the following two tables:

| Type | 1 | 2 | 3 |
|---|---|---|---|
| Structure 1 | Layered structure: thermo-bonded Airlaid with laminated nonwoven | 40% polyester short cut fiber, 60% SAF | Bicomponent fiber of a SAF and a thermoplastic material |
| Structure 2 | Bicomponent fiber of a SAF and a thermoplastic material + fluff pulp | Needle felt | Carded thermobonded nonwoven |
| SAF fiber type | 101/6/10 | 102/52/10 | 102/52/10 |
| Weight (g/cm²) | 560 | 540 | 1000 |
| Thickness (mm) | 6 | 5.4 | 20 |
| Absorption capacity | 31.2 l water/m² | >20 g water/g | >16 g water/g or 16.000 g water/m² |
| Absorption capacity under pressure (0.9% NaCl solution/m² at a pressure of 0.2 psi) | 16 | | |
| Total content of SAP (% w/w) | 18 | 40 | 50 |

| Type | 4 | 5 | 6 |
|---|---|---|---|
| Structure 1 | Layered structure: thermos-bonded Airlaid with laminated nonwoven | 25% polyester short cut fiber, 75% SAF | 40% polyester short cut fiber, 60% SAF |
| Structure 2 | Bicomponent fiber of a SAF and a thermoplastic material + fluff pulp | Needle felt | Needle felt101/6/10 |

-continued

| SAF fiber type | 101/6/10 | 102/52/10 | 102/52/10 |
|---|---|---|---|
| Weight (g/cm²) | 350 | 150 | 180 |
| Thickness (mm) | 3.5 | 2.4 | 3.8 |
| Absorption capacity | 19.5 l water/m² | >25 g 0.9% NaCl$_{aq}$/g | >17 g water/g or 6,400 g water/m² |
| Absorption capacity under pressure (0.9% NaCl solution/m² at a pressure of 0.2 psi) | 16 | | |
| Total content of SAP (% w/w) | 18 | 75 | 60 |
| Tensile strength (N/5 cm) | | 16 ± 13 | 16 ± 13 |
| Elasticity (%) | | 60 ± 18 | 60 ± 18 |

Further preferred layers with superabsorbent polymers exhibit characteristics as shown in the following table:

| Type | 1 | 2 | 3 | 4 | 5 | 6 | 7 | 8 |
|---|---|---|---|---|---|---|---|---|
| Weight (g/m²) | 430 | 300 | 150 | 5 | 100 | 120 | 140 | 440 |
| Thickness (mm) | 1.3 | 1.2 | 0.9 | 0.7 | 0.7 | 0.76 | 1 | 1.2 |
| Liquid retention (g/g) | 28 | 33 | 28 | 15 | 25 | 28 | 11.5 | 38 |
| Tensile strength (N/5 cm) | 25 | 55 | 20 | 20 | 20 | 20 | 15 | 20 |
| Uptake capacity (g/g) | 45 | 200 | 50 | 20 | 40 | 50 | 28 | 55 |

Foams

In an alternative embodiment the liquid absorbing layer comprises or consists of a foam, being preferably an open cell foam or even an reticulated foam. They create a moist environment and provide thermal insulation to the wound. A foam layer is especially suited for use in the reduced pressure treatment. Foams can form a soft cushion and easily absorb liquid which can thereafter be released by application of reduced pressure.

Foams are generally materials with cells (open, closed, or both) distributed over their whole mass. Materials thus generally have a raw density (in accordance with DIN 53420) which is lower than the density of the basic substance.

A cell is an individual cavity formed in the manufacture of the foam which is partially or fully enclosed by the cell walls and/or cell struts.

A closed cell is usually a cell which is completely enclosed by its walls and has no connection via the gas phase with the other cells. An open cell is generally a cell which is connected with other cells via the gas phase. In the context of this application, the term open-cell means that in the foam has at least 60% open cells, preferably at least 90% open cells, even more preferably 98% open cells, in particular essentially 100% open cells with reference to the total number of cells.

The cell wall is generally taken to mean the wall enclosing the cell. The cell wall can also be referred to as the cell membrane. The cell strut is generally taken to mean the area of the cell wall which separates more than two cells. Cell struts are preferably at least 1.5 times the thickness, even more preferably at least twice the thickness of the rest of the cell wall.

A reticulated foam is taken to mean a foam which consists largely of cell struts.

In one embodiment of the invention the foam is a polymer foam preferably made from polyurethane, polyvinyl alcohol (PVA), polyester or cross-linked polyorganosiloxane. Most preferred is the use of a polyurethane foam.

Regarding the cross-linked polyorganosiloxane foam material the foam is preferably obtained by reaction by reaction of a curable mixture containing the components:

(i) a polyorganosiloxane containing one or more groups with a $C_2$-$C_6$ alkenyl group, preferably containing one or more vinyl groups, (ii) a polyorganosiloxane containing one or more Si—H groups, (iii) a foaming agent containing one or more OH groups, and (iv) an organometallic catalyst.

In a preferred embodiment the above stated component (i) contains a polyorganosiloxane in accordance with general formula (I)

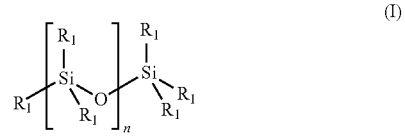

(I)

in which $R_1$ is independently $C_{1-6}$ alkyl, $C_{1-6}$ haloalkyl, aryl or $C_2$-$C_6$ alkenyl, provided that n has a value such that the viscosity of the polyorganosiloxane is in a range between 500 and 250,000 mPas and that the molecule contains at least one $C_2$-$C_6$ alkenyl group.

In a further preferred embodiment the component (ii) as stated above contains a polyorganosiloxane in accordance with the general formula (II):

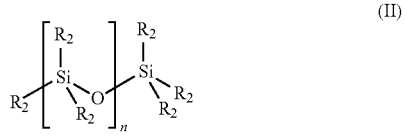

(II)

in which $R_2$ is independently $C_{1-6}$ alkyl, $C_{1-6}$ haloalkyl, aryl or hydrogen, provided that the molecule contains at least two hydrogen atoms bonded with silicon, whereby they are bonded to different silicon atoms.

For an advantageously effect within the wound care article the polymer foam of the liquid absorbing layer has a specific absorption capacity. In an preferred embodiment, the foam absorbs between 0.1 g/cm² and 1.2 g/cm² of liquid, most preferably between 0.3 g/cm² and 0.9 g/cm².

It is furthermore of advantage if the foam has a specific tensile strength and elongation. In a preferred embodiment, the foam has a tensile strength of 3-16 N/cm, most preferably of 7-9 N/cm and a tensile elongation of 120%-600%, most preferably of 170%-210%.

In a preferred embodiment the polymeric foam is used in a dry condition.

In a further preferred embodiment the polymeric foam layer has a thickness of 1 to 15 mm, preferably from 2 to 10 mm, and most preferably from 3 to 7 mm.

In another embodiment of the invention the polymeric foam is provided with further antioxidant, bactericidal or bacteriostatic agents as disclosed within the present application.

Intermediate Occlusive Layer

According to the invention the wound care article comprises an intermediate occlusive layer.

The occlusive layer of the invention is impermeable to fluids and in a preferred embodiment also impermeable to gases.

In a preferred embodiment the occlusive layer is a polymer layer which consists of one of the following polymers: polyvinylidene chloride, polyethylene terephthalate (PET), oriented polypropylene (OPP), biaxially oriented polypropylene (BOPP), oriented polyamide (OPA), biaxially oriented polyamide (BOPA), or a multi-layer high barrier film, preferably selected from the group consisting of polyethylene/ethyl vinyl alcohol copolymer/polyethylene (PE/EVOH/PE), PP/EVOH/PP, PP/EVOH/PE, polyamide/polyethylene (PA/PE), PE/PA/PE, PP/PA/PE, PA/EVOH/PA/PE and PP/PA/EVOH/PA/PE, EVOH/OPP, EVOH/BOPP, EVOH/OPA, EVOH/BOPA and PVDC/PET.

In another embodiment the occlusive layer is a metal film, e.g. an aluminium film, or a metallized polymer film.

Active Agent-Releasing Layer

According to the invention the wound care article comprises a bottom active-agent releasing layer.

The active agent-releasing layer of the present invention comprises an active agent that can be released by said layer to enter the wound site.

In a preferred embodiment the active agent releasing layer is a non-woven. In a more preferred embodiment the active agent releasing layer, being preferably a non-woven, is made from a material selected from the list consisting of viscose, polypropylene, polyethylene, polyethylene terephthalate, superabsorbent fibres and combinations thereof In another embodiment the active agent releasing layer is a hydrogel, and preferably comprises superabsorbent fibres.

In a further preferred embodiment the active agent releasing layer comprises or consists of a non-woven comprising superabsorbent fibers.

The therapeutic gas is preferably selected from the list consisting of oxygen, ozone, carbon dioxide, nitric oxide or combinations thereof.

In a preferred embodiment of the invention the therapeutic gas is nitric oxide.

In case that the active agent is a gas, the wound care article of the invention preferably comprises a gas-permeable layer oriented towards the wound area.

The gas-permeable layer, such as a membrane, is devised to regulate the diffusion of the gas, being preferably NO, out of the wound care article towards the skin. Thus, the gas-permeable layer is configured to regulate the gas transfer speed from the patch to the user's skin. Furthermore, the membrane may be chosen in dependence on the NO generating system in the patch. For instance, the NO generating system may comprise NO donor compounds or degradation products that are toxic, irritant, or non-toxic. The gas permeable layer may be chosen in dependence of this level of skin compatibility, i.e. different membranes may be suitable. In this manner, the wound care article may be provided in a cost-efficiently manner while maintaining patient comfort.

In the case of good communication allowed across the gas-permeable layer, e.g. when the gas-generating system is non-toxic, the gas-permeable layer may be made in form of a membrane of nonwoven or porous materials that permit fluid transport. For example, the NO released from the NO donor may be transported dissolved in the fluid across the membrane to the skin. In the case of medium communication is allowed across the gas-permeable layer, e.g. when the gas-generating system (e.g. the NO donor or its activation agents) is irritant, and in case the activation fluid is water, a high moisture vapour transfer rate (MVTR) material, such as a micro porous membrane or a monolithic partially hydrophilic block polymer membrane, may be provided in some embodiments. Such membranes hydrophilic parts will quickly be filled with water and the gas, being preferably NO may be transported dissolved in the water across the membrane. In the case of low communication is allowed across the gas-permeable layer, e.g. when the gas-generating system is moderately toxic, it is necessary to hinder medium to large components from traveling across the gas-permeable layer. In case the fluid is water, a medium/low MVTR material is chosen that is slowly be filled with water. NO as a released gas is mainly transported together with the water. In the case no communication is allowed across the gas-permeable layer, e.g. when the gas-generating system is toxic, it is necessary to totally separate the interior of the wound care article and especially the active agent-releasing layer from the skin with regard to the gas-generating systems. The material of the gas-permeable layer is chosen such that no liquid communication is allowed across the membrane. Any liquid transport is fully prevented by the membrane. In case the fluid is water, at least one layer is provided in the membrane, which is hydrophobic, in order to hinder water transport across the membrane. In this case, the gas, being preferably NO transported up to the hydrophobic layer dissolved in the water. From the hydrophobic layer, withholding the fluid water, the gas, being preferably NO diffuses from the water through the hydrophobic layer towards the skin.

Suitable membrane materials are Silicone, co-polyester, polyolefins, polyimides, polysulfones, polyamides, EVA, PTFE, as well as PUR that has sufficient permeability to be used, depending on configuration and material with regard to providing selectively fluid or water permeation or not. Hitherto membranes have been permeable for substances that are made of much larger molecules than gases such NO.

In a preferred embodiment an NO permeable layer is configured to be selectively permeable for nitric oxide molecules. In this manner the NO permeable layer provides for an efficient protection barrier preventing unwanted NO donor compound components, to be transferred via the NO permeable layer during the transfer of NO. Hence, the NO permeable layer not only regulates the NO release from the wound care article, is also ensures that the NO donor compound or components thereof, are only exposed to the skin if allowed, e.g. when non-toxic or non-irritant.

For hydrophobic gases a gas release membrane of hydrophobic nature is used, whereas for hydrophilic gases a gas membrane of hydrophilic nature is used.

In one embodiment of the invention, the gas release membrane has a thickness between and 100 µm, thus representing a stable membrane with sufficient control of the gas release.

In another embodiment, the gas release membrane has a water Vapour Transmission Rate of between 10-120 g/m²·24 h (measured at 37° C., 30% relative humidity).

In a further embodiment of the invention the active agent-releasing layer comprises different reactants that are separated from each other by a barrier, whereby breaking or removing the barrier allows a mixing of reactants in order to generate the active agent.

In a preferred embodiment a first reactant is a NO donor and the second reactant is a reducing agent or a proton donor.

NO Donor

In one embodiment of the invention the NO donor is selected from the group consisting of inorganic nitrite salts, alkyl nitrites such as isopentyl nitrite, diazeniumdiolated organic compounds, trans[RuCl([15]aneN4)NO]2+, Nitrosyl-ligands, 6-nitrobenzo[a]pyrol, S-nitroso-glutathione, S-nitroso-thiols, S-nitroso-N-acetyl-D-penicillamine (SNAP), L-arginine, L-citrulline, nitroglycerin (GTN), isosorbide 5-mononitrate (ISMN), isosorbide dinitrate (ISDN), pentaerythritol tetranitrate (PETN), erythrityl tetranitrate (ETN), amino acid derivatives such as N-hydroxy-L-arginine (NOHA), N.sup.6-(liminoethyl)lysine) (L-NIL), L-N.sup.5-(1-iminoethyi)ornithine (LN-NlO), N.sup.a-methyl-L-arginine (L-NMMA), S-nitroso glutathione (SNOG), S,S-dinitrosodithiol (SSDD), 2-[(pyridin-3-ylcarbonyl)amino]ethyl nitrate (nicorandil), sodium nitroprusside (SNP), S-nitroso-N-acetylpenicillamine (SNAP), [8-[2-hydroxy-3-(propan-2-ylamino)propoxy]-3,4-dihydro-2H-chromen-3-yl] nitrate (Nipradilol), 3-morpholino-sydnonimine (SIN-1), molsidomine, DEA-NONOate (2-(N,N-diethylamino)diazenolate-2-oxide), spermine NONOate (N-[4-[1-(3-aminopropyl)-2-hydroxy-2-nitrosohydrazino] butyl-1,3-propanediamine), 3-(5'-hydroxymethyl-2' furyl)-1-benzyl indazole (YC-1), nitroaniline derivatives, 2-methyl-2-nitrosopropane, imidazoyl derivatives, nitrate ester, hydroxyl nitrosamine, hydroxylamine and hydroxyl urea, and combinations thereof.

In a preferred embodiment inorganic nitrite salt is selected from the group consisting of $LiNO_2$, $NaNO_2$, $KNO_2$, $RbNO_2$, $CsNO_2$, $FrNO_2$, $Be(NO_2)_2$, $Mg(NO_2)_2$, $Ca(NO_2)_2$, $Sr(NO_2)_2$, $Ba(NO_2)_2$, and $Ra(NO_2)_2$ and combinations thereof.

Reducing Agent and Proton Donor

In one embodiment of the invention, the reducing agent is selected from the group consisting of ascorbic acid, cysteine, glutathione, penicillamine, N-acetylcysteine, iodine, hydroquinone, mercaptosuccinic acid, thiosalicylic acid, methylthiosalicylic acid, dithiothreitol, dithioerythritol, 2-mercaptoethanol, $FeSO_4$, and $FeCl_2$, and combinations thereof.

In a preferred embodiment the NO as an active agent is produced by the reaction of a NO donor with a reducing agent capable of forming a transient nitrosyl complex. NO precursors include nitrite, nitric acid, and nitrate. In some embodiments, a NO releasing polymer as described in WO 2008/116497, WO 2008/116925 and EP 1871433 can be used as a NO precursor that releases NO when contacted with a proton donor. In these cases, NO eluted from the polymer is initiated by contact with water or other proton donor and the eluted NO forms a complex with a reducing agent/complexing agent or a complexing agent.

Examples of chemical reactions for producing NO include:

$$3\ NaNO_2 + 3\ FeSO_4 + 3\ H_2O \rightarrow Fe_2(SO_4)_3 + 3\ NaOH + FeOH_3 + 3\ NO \quad (1)$$

$$2\ NaNO_2 + 2\ FeSO_4 + 2\ H_2SO_4 \rightarrow Fe_2(SO_4)_3 + 2\ NaHSO_4 + 2\ H_2O + 2\ NO \quad (2)$$

$$2\ NaNO_2 + 2\ KI + 3H_2SO_4 \rightarrow I_2 + 4\ KHSO_4 + 2\ NO \quad (3)$$

$$8\ HNO_3 + 3\ Cu \rightarrow 3\ Cu(NO3)_2 + 4\ H_2O + 2NO \quad (4)$$

$$2\ NaNO_2 + 2H^+ \rightarrow 2HNO_2 \rightarrow N_2O_3 + H2O, N_2O_3 + AA \rightarrow NO + \text{ascorbyl radical} \quad (5)$$

$$NO_2^- + H^+ \rightarrow HNO_2, NO_2^- + HNO_2 \rightarrow N_2O_3 + OH^-,\ N_2O_3 \rightarrow NO_2 + NO \quad (6).$$

(AA=ascorbic acid)

Examples of reducing nitrosyl complex forming agents include, but are not limited to, Cu, Cu(I), V(III), Mo(VI), Fe(II), I⁻, Ti(III), Co(II), Mn(II), and Cr(III) and their salts. The NO precursor and reducing agent may be in the form a solid, aqueous solution or gel. Some reducing nitrosyl complex forming agents, such as Fe(II), change colour when they form nitrosyl complexes, allowing the activation of NO production and depletion to be monitored.

The above reactions may advantageously take place in an environment excluding atmospheric oxygen. Nitrite ($NO_2^-$) or other NO precursor and reducing nitrosyl complex forming agents (CA) are initially present in the reaction in a predetermined ratio ($NO_2^-$):(CA), which can be varied so as to result in faster or slower nitric oxide release-rates. If ($NO_2^-$)=1, then (CA), is varied between 1.5 and 30 for NO release to be controlled by complex formation. The presence of an excess of reducing/complexion agent ensures that unreacted reducing/complexing agent remains after NO production to complex with NO. For example, ferrous ion reacts with nitrite to form NO and ferric ion. Ferric ion does not form a transient complex with NO. Unreacted ferrous ion, however, is available because the reducing/complexing agent ferrous sulfate is present in excess. In the case of nitrite and ferrous sulfate, the transient complex formed is $[Fe(H_2O)_5(NO)]^{2+}$. The transient NO complexes serve to control the release of NO by delaying NO release from the device in a predictable manner.

The nitrite concentration is preferably between 0.1 and 100 µmol/cm² dressing area and more preferably from 0.5 to 300 µmol/cm² dressing area. The reducing/complexing agent may be stabilized by the presence of an acid. Acid is not required for the production of NO from nitrite and a reducing agent, for example, and large changes in absolute and relative acid concentrations of acid in these reactions do not alter the rates of NO release from a NO delivery device according to the present invention. The presence of acid, however, stabilizes reducing agents such as ferrous sulfate, particularly if atmospheric oxygen is present. Acid is not necessary if the device is prepared in a reduced oxygen environment. Acids useful for producing NO and/or stabilizing reducing agents include acetic acid, lactic acid, tartaric acid, ascorbic acid, citric acid salicylic acid, HCl, HBr, $H_2SO_4$, $HNO_3$, $HClO_4$, HI, and combinations thereof. By the use of the methods described herein, it is possible to produce NO delivery devices that produce and release NO containing less than 5% of impurities, less than 2% of impurities, and less than 0.5% of impurities by weight.

In a further embodiment of the invention the proton donor is selected from the group consisting of $H_2SO_4$, HCl, HBr, HI, $HNO_3$, acetic acid, lactic acid, tartaric acid, ascorbic acid, citric acid, salicylic acid, and combinations thereof.

In one embodiment this active agent is a cytokine and/or a chemokine. For example, the active agent-releasing layer may contain at least one compound from a group including fibroblast growth factor-2 (basic FGF), transforming growth factor-beta (TGF-beta) platelet derived growth factor (PDGF), cartilage derived growth factor (CDGF), epidermal growth factor (EGF), transforming growth factor alpha (TGF-alpha), thrombospondin, osteopontin, angiotensin converting enzyme (ACE), bone morphogenetic protein (BMP), NGF (nerve growth factor), tumor necrosis factor alpha (TNF-α), acidic fibroblast growth factor (aFGF), hepatocyte growth factor (HGF), insulin-like growth factors 1 and 2 (IGF-1 and IGF-2), stromal derived factor 1 alpha (SDF-1 alpha), ciliary neurotrophic factor (CNTF), neurotrophin-3, neurotrophin-4, neurotrophin-5, pleiotrophin protein (neurite growth-promoting factor 1), midkine protein (neurite growth-promoting factor 2), brain-derived neurotrophic factor (BDNF), tumor angiogenesis factor (TAF), corticotrophin releasing factor (CRF), interleukin-8 (IL-8), granulocyte-macrophage colony stimulating factor (GM-CSF), growth differentiation factor-9 (GDF9), myostatin (GDF-8), and/or vascular endothelial growth factor (VEGF).

It is preferred that the active agent is released slowly and sustained over at least one day, or over at least 3 days or over at least 5 days, or over at least one week, or over at least two weeks, or over at least 3 weeks, or over at least one month. Typically the active agent is released directly to the target tissue in the body.

Further Active Agents

According to the invention the active agent as contained within the active-agent releasing layer can be not only a therapeutic gas but also a liquid or solid agent as described in the following. Notably, these further active agents can be present as sole active agent or in addition to the therapeutic gas disclosed above, and thereby preferably in addition to NO.

In a further embodiment the active-agent releasing layer comprises at least one hemostypic or haemostatic agent. These agents stimulate haemostasis, thereby supporting the healing process. Suitable examples for hemostatics are vitamin K, coagulating factors (e.g. factor VIII, factor IX), trans-4-aminomethyl-cyclohexan-carboxylic acid, epinephrine, adrenochrome, thrombin, fibrin, fibrinogen, cholesteryl sulfate, Extracts from pharmaceutical chamomile (*Chamomilla recutita*), leave extracts from dioecious nettle (*Urtica dioica*), carboxymethyl chitosan, polycarbophils (e.g., calcium carbophil), sephadex or debrisan.

In another embodiment, active-agent-releasing layer may contain analgesic substances which are preferably combined with a therapeutic gas as described above. For this, essentially all of the substances that are listed in the main group of the so-called "red list" may be considered. Particularly preferable thereby are specifically anti-inflammatory substances such as, so-called COX inhibitors or NSAID (non steroidal anti-inflammatory drugs), as well as, for example, propionic acid derivatives, such as naproxen, ibuprofen, ketoprofen, fenoprofen, flurbiprofen, dexibuprofen, or tiaprofenic acid, acetic acid derivatives such as diclofenac, alclofenac, etodolac, aceclofenac, sulindac, or indometacin, heterocyclic acetic acids such as ketorolac, arylalkanoic acids such as tolmetin, N-phenylacetic acids such as mefenatnic acid or flufenamic acid, salicylates such as acetylsalicylic acid (aspirin), salicylic acid, or diflunisal, pyrazolone derivatives such as phenylbutazone, oxicam derivatives such as piroxicam, tenoxicam, meloxicam, or lomoxicam, enolic acid derivatives such as aminopyrine or antipyrine, phenols such as acetaminophen and similar items. In addition, there are the COX-2-inhibitors such as rofecoxib, lumiracoxib or celecoxib.

Furthermore, substances which are not anti-inflammatory may also be used as analgesic substance, such as, for example, an opiate, a local anaesthetic such as lidocaine, mepivacaine, prilocaine, procaine, syntocaine, tetracaine, gingicaine, articaine, bupivacaine, butanilicaine, chloroprocaine, or for example, polidocanol.

In addition, the active-agent releasing layer may contain anti-inflammatory substances that, as the case may be, exhibit secondary analgesic properties, such as, for example, aside from the above mentioned, which in part are also anti-inflammatory analgesics, hormones, particularly cortisone and corticoids, specifically glucocorticoids (e.g. cortisone, cloprednol, prednisone, prednisolone, methylprednisolone, deflazacort, fluocortolone, triamcinolone, dexamethasone, betamethasone) and mineralocorticoids (e.g. aldosterone, desoxycorticosterone, fludrocortisone).

As a rule, it may be beneficial to overdose the wound beyond the acute treatment needs with said substances or complexes of substances-particularly the nutrients, disinfectants and/or, as the case may be, the analgesics as, for example, portions of the substances will remain in the dressing. This overdosing serves, however, not to resolve the overall insufficiency of the nutrients in a patient, or to prevent systemic sepsis, because a systemic effect, as is mentioned above, is neither intended nor desired. Nevertheless, the selected dosage may be higher than the dosage, as will be explained in the following, which is the recommended oral or enteral daily dosage. This is useful in particular because, for example, in the end the application of the composition in a dressing should frequently remain on the dressing for a longer period of time.

If it is the case that compositions are used, for example, that contain a dietetic composition, it is particularly intended that the amount used, for example, per wound care product (e.g. foam pad, or dressing containing SAP) lies in the range between 10% and 200% of the DGE (Deutsche Gesellschaft für Ernährungsmedizin [German Society for Nutritional Medicine]) recommended daily dosage. It is particularly preferred that this lie in the range between 30% and 100% of the recommended daily dosage.

The said composition can, thereby, be incorporated in the active-agent releasing layer in advance. Alternatively, the composition may be incorporated in said layer in its dehydrated form.

In another embodiment, the active-agent releasing layer contains one or more substance(s) which are selected from the group containing orthomolecular nutrients, nutraceuticals, phytochemicals, antioxidants, growth factors, petroleum based blistering compounds, methylxanthines, tallins, tacrolimus, pimecrolimus, ATP, urea, sympathomimetic drugs, parasympatholytics, activated carbon, octenidine, polyhexanide, homeopathic remedies, Q|O, thickening agents, karaja, pectin, agar, aloe vera, haemostatics, animal saliva such as maggot or canine saliva, spider web proteins, collagen, hygroscopics, glycerin, biofilm harming substances, triacetin, zinc oxide, light absorbing components, odor inhibitors, gelling agents, exudation promoting substances, swelling reducing agents, radical scavengers, and/or antioxidants. Most of these components belong to the definitions given above of nutrients, disinfectants, and/or proteases inhibiting substances or complexes of substances. Said substances are included in the active-agent releasing layer as sole or main active agent or are preferably combined with a therapeutic gas, which is preferably nitric oxide.

Antioxidants are substances which prevent the oxidation of sensitive molecules, particularly DNA and proteins. They usually function as radical scavengers. Antioxidants can be categorized as "antioxidants", "reducing substances" and "antioxidants with synergetic effects." A definition for the so-called true antioxidants is the mechanism whereby the chain reaction resulting from the scavenging of free radicals is blocked.

Examples of such antioxidants are BHA and BHT. In contrast to this, for example, ascorbic acid functions as a reducing agent by allowing lighter oxidation than that of the molecule being protected, thereby protecting said. Sodium EDTA belongs to this last group of synergistic antioxidants, for example, in that it enhances the antioxidant effect by bonding with metal ions.

In the framework of the present invention, the following antioxidants are to be taken into consideration: Antioxidants belonging to the vitamin E group, carotenoids, particularly lycopene and B-carotene, glutathione, transferrin, albumin, ceruloplasmin, hemopexin, haptoglobin, antioxidant enzymes, particularly superoxide dismutase (SOD), glutathione peroxidase (GPX), and catalase, tin chloride, ascorbic acid (vitamin C) and its derivative sodium L-ascorbate, calcium L-ascorbate, isoascorbic acid, sodium isoascorbate, and ascorbyl palmitate, butylated hydroxyanisole, butylated hydroxytoluene, calcium disodium EDTA. gallates, particularly propyl gallate, octyl gallate, and dodecyl gallate (lauryl gallate), lecithin, lactic acid, polyphosphates such as diphosphate, triphosphate, and polyphosphate, sulfur dioxide, sodium sulfite, sodium bisulfite, potassium sulfite, calcium sulfite, calcium bisulfite, potassium bisulfite, selenium, tocopherol (vitamin E), alpha-tocopherol, gamma-tocopherol, delta-tocopherol, tin II-chloride, citric acid as well as sodium citrate, calcium citrate, and reducing agents such as acetylcysteine.

Methylxanthines are a group of alkaloids, which are usually used as mild stimulants as well as for treating bronchial asthma. They include caffeine, theophylline, and theobromine. Xanthines are purine derivatives. They have a constricting effect and tend to reduce swelling, so that, as the case may be, oedema in the affected area is reduced, and nutritional, disinfecting and/or proteases inhibiting substances are not diluted unnecessarily.

Tannins function as astringents, i.e. they serve to reduce oedema, are ant-inflammatory, antibacterial, antiviral, and neutralize toxins.

Tacrolimus (also FK506 or FK-506) is a macrolide from the bacteria *Streptomyces* tsukubaensis. Tacrolimus is used as, among other things, a selective immuno-suppressive against rejection reactions in organ transplants. Tacrolimus is both immuno-suppressive and antimicrobial. Its effects can be compared with those of the polypeptide cyclosporine, but may be used in smaller doses. Tacrolimus intervenes in the metabolic process of T-cells, and inhibits their activity. It bonds to the cytosolic receptor, a so-called immunophilin within the target cell. The complex comprised of immunophilin and tacrolimus adheres to the serine/threonine-protein phosphatase calcineurin. Calcineurin is thereby rendered inactive. The same basically applies for the substance tacrolimus.

ATP is a nucleotide, formed from the triphosphate of the nucleoside adenosine, and as such is an energy rich component of the nucleic acids DNA and RNA. ATP is however also the universal form of directly available energy in every cell and at the same time an important regulator of energy providing processes. ATP can be released from energy stores (glycogen, creatine phosphate) as it is needed. By adding ATP to the composition of the invention, an energy source free of glucose is made available, and is particularly useful in treatments where diabetes is present for improving the energy balance of the cells.

Urea has a high capacity for bonding with water and also exhibits keratolytic properties. In addition, it serves as a source of moisture for fighting atopic eczema and lichen diseases and is therefore particularly suited for use in a composition in accordance with the invention.

Necrolytes are agents which eat away at necrotic tissues. These may, for example, be the petroleum based blistering compounds described here. Other possible necrolytic agents are, for example, urea or animal saliva, both of which will be described below.

Sympathomimetics have a stimulating effect on the sympathetic portion of the autonomic nerve system. They affect an increase in blood pressure and pulse rate, a dilation of the bronchial passage, an overall improvement in performance and an increase in energy consumption. In combination with the composition of the invention, these substances reduce swelling as well as edema.

Parasympatholytics are medicines which counteract the action of the parasympathetic nervous system. The therapeutic use of parasympatholytics is complicated by insufficient organ selectivity. In this manner atropine, as a medicine for chronic obstructive bronchitis, promotes not only dilation of the bronchial tract, but also stimulates the heartbeat, dilation of the pupils, and a contraction of the smooth muscles. Use of these substances has a comparable effect to the sympathomimetics described above.

Activated carbon is a fine-grained carbon with a large internal surface, which is used in, among other things, chemistry, medicine, water and waste treatment as well as ventilation and air conditioning technology. When incorporated in a composition in accordance with the invention, it can contribute to bonding with toxins arising from metabolic processes and germs, and thereby, cleansing of the affected area.

Q10 or coenzyme Q10 is a quinone derivative with lipophilic terpenoid side chains, structurally related to vitamin and vitamin E. Coenzyme Q 10 is an essential electron and proton vector between the complex I or complex II and the complex III of the respiratory chains and can support the energy metabolism of the cells in the affected area through resorption with nutrients in the framework of a composition in accordance with the invention.

Thickening agents are added to solutions, which preferably are aqueous solutions, in order to increase their viscosity. They are mainly able to bond with water. Through extraction of unbonded water, the viscosity is increased. After a certain point has been reached, characteristic for each type of thickening agent, additional moisturizing effects occur which usually lead to an over proportional increase in viscosity. Thickening agents in combination with the composition of the invention allow for an adaptation to the surface of the wound, and a maximization of the resorption surface.

Suitable thickening agents are, for example, karaya (Indian tragacanth, karaya gum, E 416), a natural gum comprised of carbohydrates and galacturonic acids (secretion of the Indian sterculia tree), alginic acid, agar, carrageen, locust bean gum, guar gum, tragacanth, gum Arabic, Xanthan gum, karaya, tara gum, gellan, pectin, cellulose, cellulose ether, carboxymethyl cellulose, hydroxypropyl cellulose, hydroxypropyl methylcellulose, methyl cellulose, methyl ethyl cellulose, modified starch, egg yolk, roux, sago, and starch.

Pectins are vegetable polysaccharides, or specifically polyuronides, which for the most part are comprised of α-1.4-glycosidically linked D-galacturonic acid units. Many microorganisms are able to metabolize pectins. Due to their ability to create gels, pectins may also be used as a thickening agent in the manner indicated above. In addition, they are capable of functioning as chelating agents in the detoxification of heavy metal poisoning, and are therefore particularly suited for use in the framework of a composition in accordance with the invention.

Aloe vera is a plant from the aloe family which is produced in a gel of the same name, also called acemannan, having a long chain polysaccharide. This substance stimulates the immune system in in-vitro experiments, protects the cell membranes, and is antibacterial, antiviral, and antimycotic. This substance is absorbed into the body particularly well through the gastro-intestinal tract, and can also be used, however, in the affected area. In addition, aloe vera contains minerals (calcium, magnesium, zinc, selenium, and others), vitamins, amino acids, and secondary plant substances (flavonoids). The term "aloe vera" for the purposes of the present invention, may also refer to aloe vera extracts, the substances of which may be more easily absorbed by cells in the affected area.

Furthermore, it may be intended that the composition of the invention also contain swelling reducing substances such as, for example, red eyebright (Euphrasia *officinalis*) extract, common sage (*Salvia officinalis*) or cowslip (*Primula veris*), vasoconstrictors such as oxymetazoline hydrochloride or xylometazoline hydrochloride or anti-oedemas. These may be helpful in reducing swelling in the affected area and to make oedematous fluid available, in order that they may be absorbed by an absorbent dressing.

Furthermore, it may be intended that the composition of the invention contain light absorbing components. These help to prevent the loss of structural integrity in light sensitive components (e.g. zinc oxide, vitamins).

Pigments, such as titanium dioxide for example, are particularly good components for light absorption. These can be incorporated in the sheathing or together with other components in one of the layers of the wound care product of the invention. In addition, they may be included in the packaging of the wound care product. Said may, however, be stored in the dark in general, in order to protect the contents contained therein from light.

Odour inhibiting substances absorb malodorous substances, restrain them, or prevent their existence, thereby improving the quality of life of the patients treated with the composition of the invention. These may be, for example, activated carbon, herbal extracts, perfumes and similar items.

Examples for odour inhibiting substances which can be used for the wound care article of the invention are cyclodextrin, activated carbon which can be present as powder, granulate, pellet, fiber, tissue etc., ricinol, ricinoleic acid and salts thereof, especially zinc salts, ricinol derivatives, zeolites, dispersions of organic nitrogen compounds, ion exchange materials as resins or granulates, diatomaceous earth, polymeric particles with high surface area, nitroimidazoles, preferably metronizadone.

In general, all of the disinfecting substances or complexes of substances have odour inhibiting properties.

Radical scavengers deactivate free radicals, which otherwise place biological tissue under oxidative stress, and initiate chain reactions which can generate damage to cells and tissues, particularly changes in the cellular DNA. These may be, in particular, epigallocatechin gallate, superoxide dismutase, glutathione peroxidase, vitamin A, vitamin C, vitamin E, coenzyme Q10 and anthocyanins. Bilirubin and uric acid are also able to neutralize free radicals, as well as the hormone melatonin. Radical scavengers are also frequently antioxidants. Particularly ideal thereby is notably the combination of vitamin C and vitamin E. A combination of this sort exhibits a particularly synergistic effect in regard to the antioxidative effect.

Furthermore, it is particularly intended that there be one or more vitamins, selected from the group containing vitamin B12, vitamin D, vitamin C vitamin B1, vitamin B2, vitamin B6, niacin and/or folic acid in the vitamins.

An insufficiency of vitamin B12 (cobalamin) can lead to pernicious anemia (Perniziosa), a disease in the blood count and funicular myelosis. The causes of these insufficiencies may be an insufficient supply of nutrients, as has been observed with vegans, or insufficient resorption. With insufficient receptivity in the gastro-intestinal tract, the organism is lacking the intrinsic factor in its gastric juices, a glycoprotein which is produced by the parietal cells of the stomach and is essential for the metabolism of vitamin B12. The intrinsic factor binds cobalamin in a complex protected from the digestive system, and in this manner enables it to be transported in the stomach cells whereby vitamin B 12 is able to arrive at the external tissues by bonding with other proteins (transcobalamin). A disturbance in the absorption in the terminal ileum may lead to insufficiency. Although a direct link to the healing process is unfamiliar to some sources, vitamin B12 is however one of the vitamins that typically need to be supplemented in older people.

Vitamin D is a collective name for a group of fat soluble vitamins which have numerous physiological effects. Its main representative in humans, vitamin D3 (or cholecalciferol) is a prohormone which the body produces in the skin with the aid of $UV_B$ light or can be supplied nutritionally.

Vitamin C is an organic acid. Because it is easily oxidized, it has antioxidant properties. Its most important property is the physiological function as a vitamin. Insufficiency can result in scurvy in humans. Vitamin C is a radical scavenger and exhibits antioxidant properties (it functions, in other words as a reduction agent). It is an important co-factor in the hydroxylation reaction and, among other things, enables the body to produce its own collagen thereby. Furthermore, it plays an important role in the production of amino acids. It protects other important metabolites and the genotype from oxidation through its antioxidant effects, or, respectively attacks from free radicals, which in the end means it provides protection to the cell from damage and thereby from cancer. Together with niacin and vitamin B6, vitamin C controls the production of L-carnitine, which is needed for the burning of fat in the musculature. In addition, it improves resorption of iron in the small intestine.

Thiamin or vitamin B1 is a water soluble vitamin in the B-complex having a weak, but characteristic odour and is particularly essential to the function of the nervous system.

Vitamin B 1 is necessary for the burning of carbohydrates, whereby it consumes itself as a co-enzyme. As the brain and the nerve cells are dependant on energy from carbohydrates, an insufficiency of thiamin particularly affects all brain and nerve functions.

VitaminB2 or riboflavin serves as a preliminary step for flavin co-enzymes (FAD, FMN), which play a particularly major role in oxidoreductases, for example in citric acid cycles. It assumes a central role thereby in metabolism. Riboflavin dissolves poorly in water, is sensitive to light, but is very resistant to heat. It contributes to a smooth complexion, and is involved in the regenerative mechanisms of the skin.

The phosphorylated vitamin B6 derivatives act as co-enzymes in approximately 100 enzymatic reactions. Nearly all reactions take place in amino acid metabolism. The pyridoxal phosphate (PLP or PALP) (a pyridoxine derivative) assumes another important function as a co-factor in the synthesis of δ-aminolevulinic acid, an intermediary product in the endogenous heme synthesis. Also noted is the participation of pyridoxal phosphate as a co-factor in the breakdown of animal starch (glycogens). Insufficiency results in the existence of dermatitides and growth disorders.

Niacin or nicotinic acid is a carboxylic acid of pyridine. Nicotinic acid is present in all living cells and is stored in the liver. It is an important building block of various coenzymes (NAD, NADP) and is of central importance in the metabolism of proteins, fats, and carbohydrates. It is less sensitive to heat, light, and oxygen than other vitamins in the B family. Nicotinic acid participates in the metabolism of proteins, fats, and carbohydrates. In the co-enzyme form NAD/NADP and their reduced forms NADH/NADPH, the so-called reduction equivalents, nicotinic acid is involved, for example, in the citric acid cycle and the respiratory chain. It is an antioxidant, and is involved in numerous enzymatic processes. Nicotinic acid is important for the regeneration of skin, muscle, nerves and DNA.

Folic acid is sensitive to light, oxygen, and heat, as well as being water soluble. An insufficiency of folic acid in the body affects the blood count in that it may lead to a hyperchromatic macrocytic anaemia.

Due to their metabolic-physiological characteristics, the vitamins named here, in particular either alone or in combinations, have a significant influence on the healing process, specifically because they improve the local nutritional situation, and thereby contribute to an improvement of the local cell metabolism.

Particularly preferred thereby is notably the combination of vitamin C and vitamin E. A combination of this sort has synergistic effects in particular.

In a further preferred embodiment the multi-layered wound care product is configured to achieve a delayed release of the active agent to the skin, so that the therapeutic relevant concentration of the active agent at the wound site is achieved later than 10 min and remains constant for more than 6 h, preferably more than 12 h, most preferably more than 24 h after application of the wound-care product to the wound site.

In another preferred embodiment the active agent-releasing layer is coated on the wound-facing side with an adhesive wound contact layer, the material of which is selected from one of the following materials: silicone, polyacrylate adhesive, hydrocolloid adhesive, hydrogel adhesive and polyurethane adhesive.

In another preferred embodiment, the active agent-releasing layer is coated on the wound-facing side with a non-adhesive wound contact layer, the material of which is selected from one of the following materials: silicone elastomer, hydrogel, polyethylene or cellulose.

In a preferred embodiment of the invention the active agent-releasing bottom layer has a thickness between 0.5 und 3 mm, preferably between 0.8 und 1.8 mm, und more preferably between 1.0 und 1.5 mm.

Pores or Perforations

According to the invention the active-agent releasing bottom layer and the intermediate occlusive layer are sheet-like layers, being preferably continuous sheet-like layers, having common pores or perforations which enable the passage of liquid through said layer.

According to the invention, optional further layers, positioned proximal to the liquid absorbing layer (hence towards the wound site) share these common pores or perforations.

Hence, a gas-permeable layer, being preferable a gas-releasing membrane has common pores or perforations with the active agent releasing layer and the occlusive layer.

In another embodiment, the pores, perforations or incisions are distributed in a regular manner over the area of the liquid-permeable bottom layer.

In one embodiment the pores have a triangular, rectangular, hexangular, ellipsoid or circular form, whereby a circular or square-shaped form is preferred.

In a preferred embodiment the pores or perforations each has an area of between 0.5 mm$^2$ and 100 mm$^2$. Preference is here given to values of 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99 and/or 100 mm$^2$.

In a more preferred embodiment of the invention the active agent releasing bottom layer is a grid-like structure. Hence, the sheet-like layer is equipped with perforations so that the sheet-like layer defines a grid or mesh with said perforations.

In more preferred embodiment the active agent-releasing bottom layer is a grid-like structure with trigonal, tetragonal or hexagonal meshes.

In a further preferred embodiment the perforated active agent-releasing bottom layer allows a direct contact of the overlaying layer, being preferably the bacteria-adsorbing layer, with the wound site.

In one embodiment of the invention wherein the pores or perforations account for between 1 to 50%, preferably between 5 to 20%, most preferably between 5 and 15% and especially between 7% and 10% of the area of active agent-releasing bottom layer and or the intermediate occlusive layer.

The proportion of the area of the combined pores or perforations as related to the total area of the active agent-releasing bottom layer and the intermediate occlusive layer given in % can be in the range between 20 and 80%. Preference is here given to values of 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79 and/or 80%.

In a preferred embodiment the occlusive layer exhibits a circumferential rim at the pores or perforation by projecting over the area of the underlying active agent-releasing layer.

Cover Layer

In addition the wound care product can comprise an additional cover layer. Thus, in the overwhelming majority of cases it is considered desirable for a wound dressing to be available which always has a dry outer side (i.e. side facing away from the wound or the wound contact layer). The penetration of dirt and infectious agents such as bacteria, viruses or fungi into the wound dressing from outside and in the worst case reaching the wound should also be prevented. This aim can be achieved by, for example, applying a fluid impermeable continuous protective film (hereinafter also referred to as backing film) as cover layer, whereby in a practical manner the backing film is water vapour-permeable. This layer which, as described above, should typically be impermeable to bacteria, adjoins the distal surface of liquid-absorbing layer. In an advantageous embodiment of the invention the film is only bound to the distal surface of the absorbing layer in a manner so that the film penetrate into the pores, cells or other intermediate spaces. The cover layer can be transparent to allow the level of filling or moisture in the wound dressing or the status of the wound to be assessed without having to remove the dressing. The cover layer can be filled with coloring agents. In general the film has a thickness of 10-500 μm and typically 15 to 45 μm, whereby film thicknesses of 30±micrometers are used in particular.

Films of this type are known from the prior art and comprise, for example, polyurethane-based films, such as a polyurethane film supplied by Coveris Holding S. A. (Wrexham, UK) under the product name INSPIRE®, or elastomer polyesters or mixtures of polyurethane with polyesters and/polyvinyl chloride and polyether amide block copolymers. Alternatively the backing layer can be a water-repellent and water vapour-permeable polyurethane foam with essentially closed cells.

For the purposes of the present application a polyurethane film is used as these films have good elastic properties and, in particular, exhibit form fitting properties as well as a high level of stretchability.

Suitable films have a moisture-vapour transmission rate (MVTR) of 500 to 14600 $gm^{-2}/24$ hours, typically 1000 to 2700 $gm^{-2}/24$ hours at 38° C. Higher MVTR values can be advantageous in order to delay the saturation point of the wound dressing in strongly secreting wounds. Low MVTR values can be beneficial in assuring a moist micro-environment around the wound in the case of low-secretion wounds.

On the distal surface of the absorption layer the cover layer can be laminated in any known way. For example lamination can take place by means of heat or ultrasound or by means of an additional continuous and discontinuous adhesive layer arranged between the cover layer and the absorption layer.

Depending on the intended purpose of use it may be necessary to use film of a different thickness or to combine several layers/film. Thus, it may be advantageous to provide the above-described backing film with a carrier layer in order to guarantee a particular mechanical strength and thus prevent wrinkling of the backing film. In general the thickness of the entire layer, (i.e. the film and, if applicable, the carrier and additional layer(s) should be in a range of 5 to 2000 micrometers and typically in a range of 5 to 1000 micrometers. The layer and/or the outermost film should, for practical purposes, exhibit a low coefficient of friction and, for example, not catch on textiles or clothing, rub on them or negatively interact with textiles in general.

Further Characteristics of the Wound Care Product

The dimension of the surface area of the wound care product may be selected according to the size of the wound. Typically, a wound care product of the present invention may have a surface area of from 5 $cm^2$ to 400 $cm^2$, and particularly of from 15 $cm^2$ to 200 $cm^2$, such as 100 $cm^2$. Also the shape of the wound care product according to the present invention may vary with respect to the wound to be treated, and the present invention encompasses, for example, rectangular, square-, circle- or oval-shaped wound care products. For example, the wound care product may have a rectangular shape with rounded corners as depicted in FIG. 1B.

In a preferred embodiment of the invention the wound care product has a moisture vapor transmission rate (MVTR) as measured according DIN ISO 13726-2 of more than 1000 $g/m^2/24$ h, preferably of more than 1500 $g/m^2/24$ h, and preferably of more than 2000 $g/m^2/24$ h. The parameters are a target for the test MVTR upright. And MVTR inverted is >20.000 $g/m^2/24$ h. For a wet product or hydrogel the DIN ISO 13726-2 should be adapted to measure only the vapor transmission rate and not a combination of dry loss and vapour transmission rate.

Bonding of the Different Layers

In a preferred embodiment of the invention the different layers of the multi-layered wound care article are connecting by use of an adhesive or by welding, sealing or laminating using temperature and/or pressure.

The adhesive can be chosen from pressure sensitive adhesives, such as polyacrylate adhesive, rubber-based adhesives, synthetic rubber-based adhesives or hotmelts, such as polyolefines, polyacrylates or rubber-based hotmelts.

In a preferred embodiment of the invention the top liquid-absorbing layer is connected with the underlying layer using a pressure sensitive adhesive, such as polyacrylate adhesive, rubber-based adhesive, synthetic rubber-based adhesive. This assures a solid and durable connection of the layers.

In a further preferred embodiments the adhesive is not applied over the whole of the surface but rather over a restricted area over the surface such as in stripes, a mesh-like structure or in a punctuate structure. This ensures that the different layers maintain a certain horizontal flexibility and furthermore that the exudate can pass without hindrance trough the different layer.

In a preferred embodiment of the invention the upper liquid-absorbing layer, the intermediate occlusive layer and the active agent-releasing bottom layer are bonded at the border portion or at the edges of said layers.

For gaseous active agents, occlusive intermediate layer and gas release membrane are bonded in such a way that they build a gas pouch surrounding the active agent releasing layer.

Use of the Wound-Care Product

The wound care product of the invention is particularly useful in the treatment of acute wounds, burn wounds, chronic wounds, and/or surgical wounds. The wound care product of the present invention may further be used in plastic surgery as well as for tissue engineering.

As such it can be used for the treatment of burns, partial and full-thickness wounds, pressure ulcers, venous ulcers, arterial ulcers, diabetic ulcers, chronic vascular ulcers, draining wounds, tunneled or undermined wounds, surgical wounds such as donor sites/grafts, post-Mohs surgery, post-laser surgery, podiatric dehiscence, and wound dehiscence, trauma wounds such as abrasions, lacerations, first, second, or third degree burns, and skin tears.

In the field of tissue engineering the wound care product of the invention can be used for remodelling of soft tissue, bone, cartilage, ligaments and tendons or dental applications.

For the medical use, it is required that the wound care product of the invention is provided in sterile form. This can be achieved by packaging the sterile product in a bacterial tight material with a marking on the packing that the product is sterilized. Bacterial tight materials are well known to the person skilled in art.

Adhesive Layer

In a preferred embodiment of the invention the wound care article is attached to the skin of a patient by means of an adhesive material. For these purposes, every type of physiologically acceptable adhesive can be used, in particular medical-grade adhesives. Particularly preferred are materials selected from the group containing acrylic adhesives, silicone, hydrocolloid adhesives, rubber-based adhesives (which could be based on synthetic or natural rubber), and/or latex adhesives.

Hydrocolloid adhesives generally consist of a thin polymer film that is applied to a self-adhesive substance. The carrier substance (such as synthetic rubber types, for example poly-isobutylene) contains swelling particles, which vary, depending on the manufacturer. Often, swelling particles such as carboxymethyl cellulose or sodium carboxymethyl cellulose are included. Furthermore, they are very malleable, especially when warm. Hydrocolloid adhesives are suitable for being worked into surfaces, and are specifically capable of removing moisture. They are available in paste form, but also panel or strip form.

Something similar applies to silicone materials. The degree of adhesiveness to the skin can be regulated with these materials, so that despite the adhesiveness, a non-traumatic replacement of wound dressings can be ensured.

Preferentially, such silicone adhesives can be embodied in the form of a detachable self-adhesive laminate, which comprises a structural layer, with a wound-facing side to which a hydrophobic gel is applied, for example in the form of a silicone gels, and a side facing away from the wound, which carries an adhesive for example in the form of an acrylic adhesive.

Preferentially, said adhesive material is embodied in the form of a "border dressing" as a adhesive edge, which peripherally surrounds the wound-covering element.

Said adhesive material may also be embodied in the form of a panel or a strip on which the wound-covering element is distally positioned. In this embodiment, said panel or strip may feature a central opening, which is intended to be positioned over the wound. In that embodiment, said panel or strip takes the shape of a frame. Alternatively, said panel or strip may be embodied such that a window may be cut into the panel or the strip, corresponding in shape to the outline of the wound. For these purposes, the outline of the wound may be drawn on it, and then cut out with a pair of scissors. Alternatively, a template may be used, by means of which the outline of the wound can be transferred to the panel or the strip, or by means of which [an opening corresponding to] the outline of the wound can be cut out of the panel or the strip.

Said panel or said frame consists, for example of a hydrocolloid material as described herein. Said strip consists, for example, of a so-called incision foil, which is a self-adhesive foil made out of a polymer material.

Alternatively, said panel or said frame consists of a foam material and/or a spacer fabric. Preferentially, it is worked into a gas-tight cover. On the skin-facing side, the aforementioned adhesives may be applied.

Preparation Method

In a fourth aspect the invention provides a method for preparation of the multi-layered wound care product of the invention comprising the following steps:
(a) A liquid absorbing material (such as a superabsorbent) is ultrasonically sealed into a non-woven material to form the liquid absorbing layer;
(b) The occlusive layer is bonded to one side of the active agent releasing layer by using a polyacrylate adhesive;
(c) The bilayer as formed in step (b) is provided with pores or perforations;
(d) The intermediate occlusive layer is attached onto the liquid-absorbing layer using a polyacrylate adhesive.

In an alternative embodiment of the invention the preparation of the multi-layered wound care product comprises the following steps:
(a) A liquid absorbing material (such as a superabsorbent) is ultrasonically sealed into a non-woven material to form the liquid absorbing layer;
(b) The occlusive layer is bonded to one side of the active agent releasing layer by using a polyacrylate adhesive;
(c) A release membrane representing a gas-permeable layer is bonded to the occlusive layer using heat;
(d) The trilayer as formed in step (c) is provided with pores or perforations;
(e) The intermediate occlusive layer is attached onto the liquid-absorbing layer using a polyacrylate adhesive.

BRIEF DESCRIPTION OF THE DRAWINGS

These and other aspects of the invention will be apparent from and elucidated with reference to the embodiments described hereinafter.

The invention will now be described, by way of example, based on embodiments with reference to the accompanying drawings.

In the drawings:

FIG. 1 shows a principal sketch of the wound care product according to a first embodiment in cross section (A), in a perspective view (B) or in a top view (C).

FIG. 2 shows examples for perforation patterns for the wound care product.

FIG. 3 shows the influence of the chosen perforation pattern on the absorption capacity of the wound care article.

FIG. 4 shows a principal sketch of the wound care product according to a second embodiment in a perspective view.

FIG. 5 shows a principal sketch of the wound care product according to a third embodiment in cross section.

In the Figures, like numbers refer to like objects throughout. Objects in the Figures are not necessarily drawn to scale.

DETAILED DESCRIPTION OF EMBODIMENTS

Various embodiments of the invention will now be described by means of the Figures.

Figure 1:
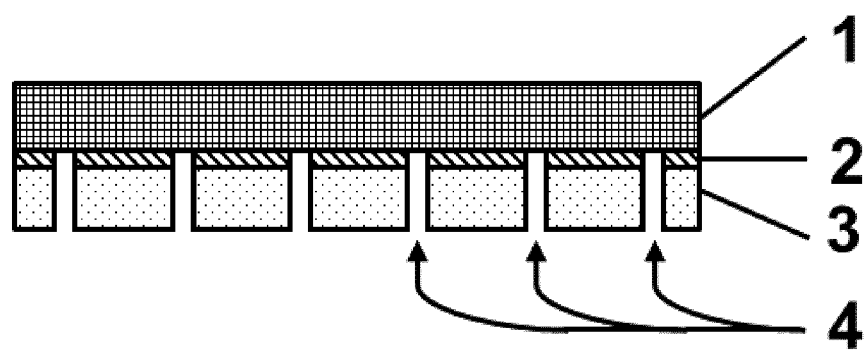
Figure 1:
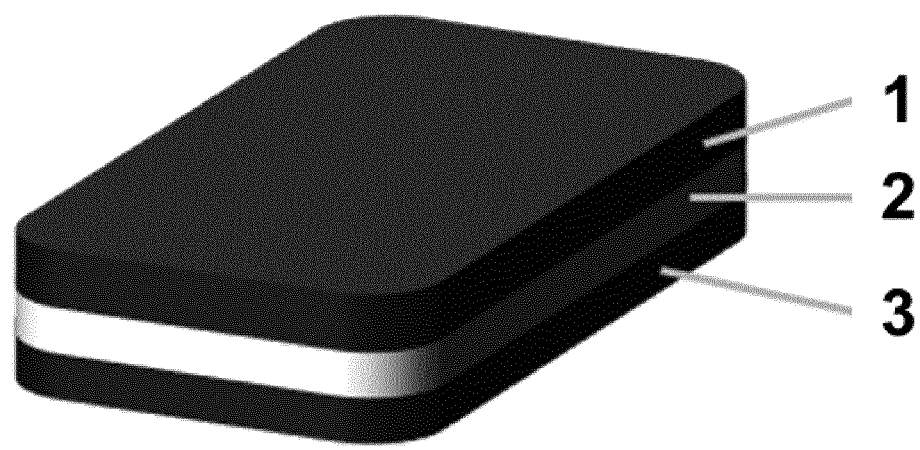
Figure 1:
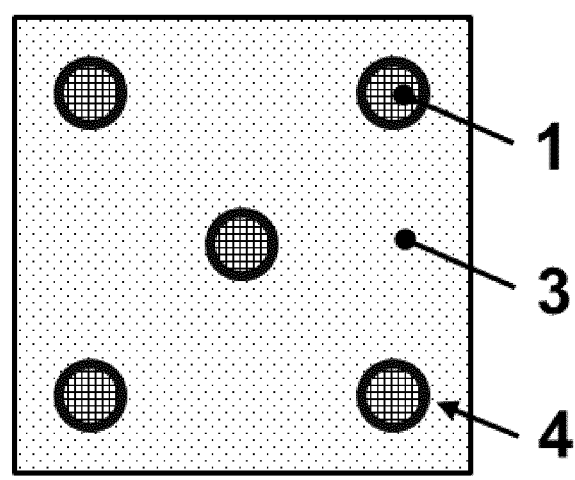

FIG. 1 shows a principal sketch of the wound care product according to a first embodiment in cross section (A), in a perspective view (B) or in a top view (C) consisting of three layers, namely the active-agent releasing layer 3, the intermediate occlusive layer 2 and the liquid-absorbing layer 1 as top layer. The wound care product is shown in a cross section/perspective view and may be applied as such to a skin wound. To this, the wound care product has a surface that will face the wound when being applied and will come in direct contact with the wound, and has an opposite surface that will face away from the wound and will thus initially not contact the wound when applied.

Figure 2:
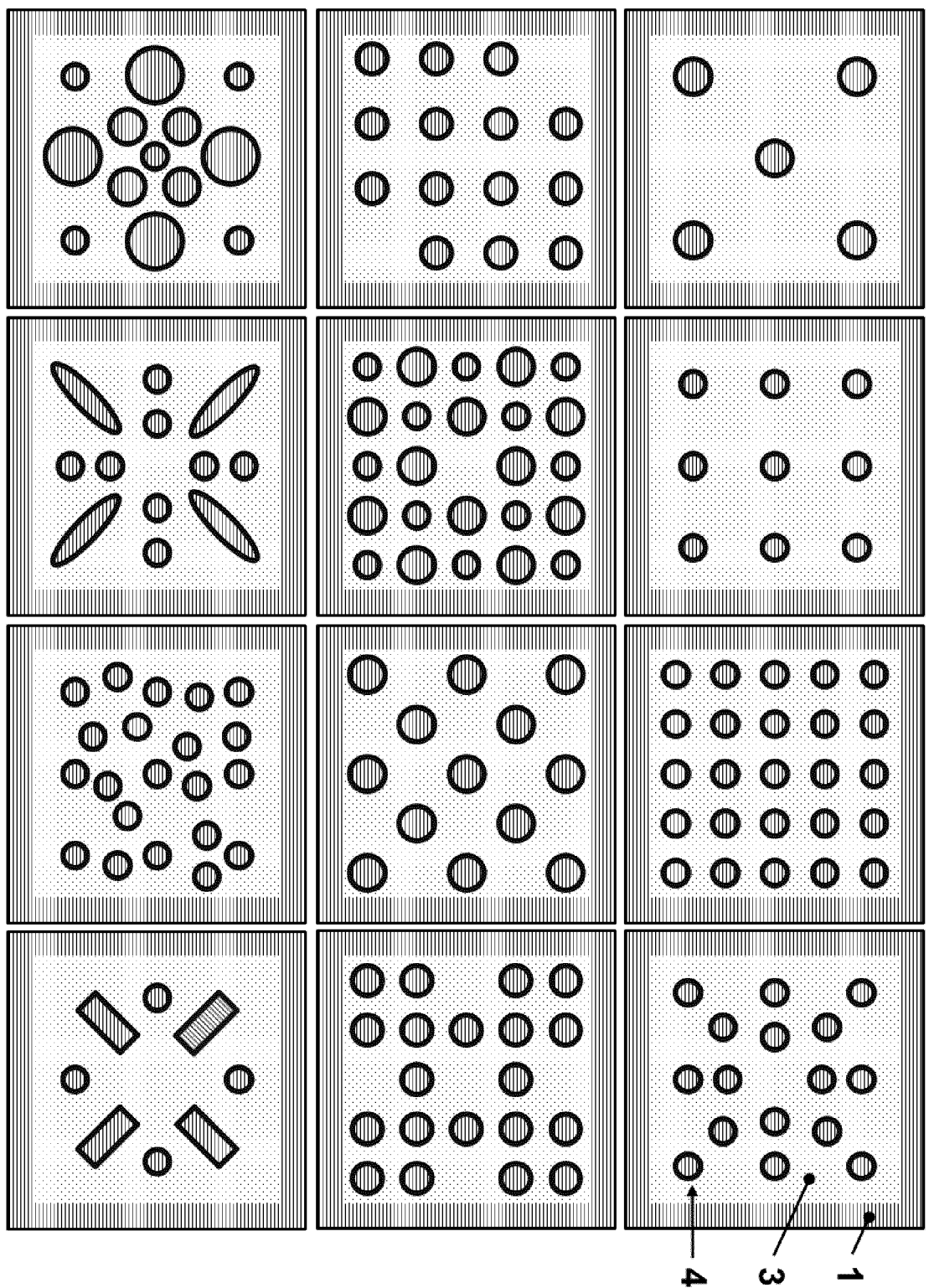

FIG. 2 shows examples for perforation patterns for the wound care product.

Figure 3:
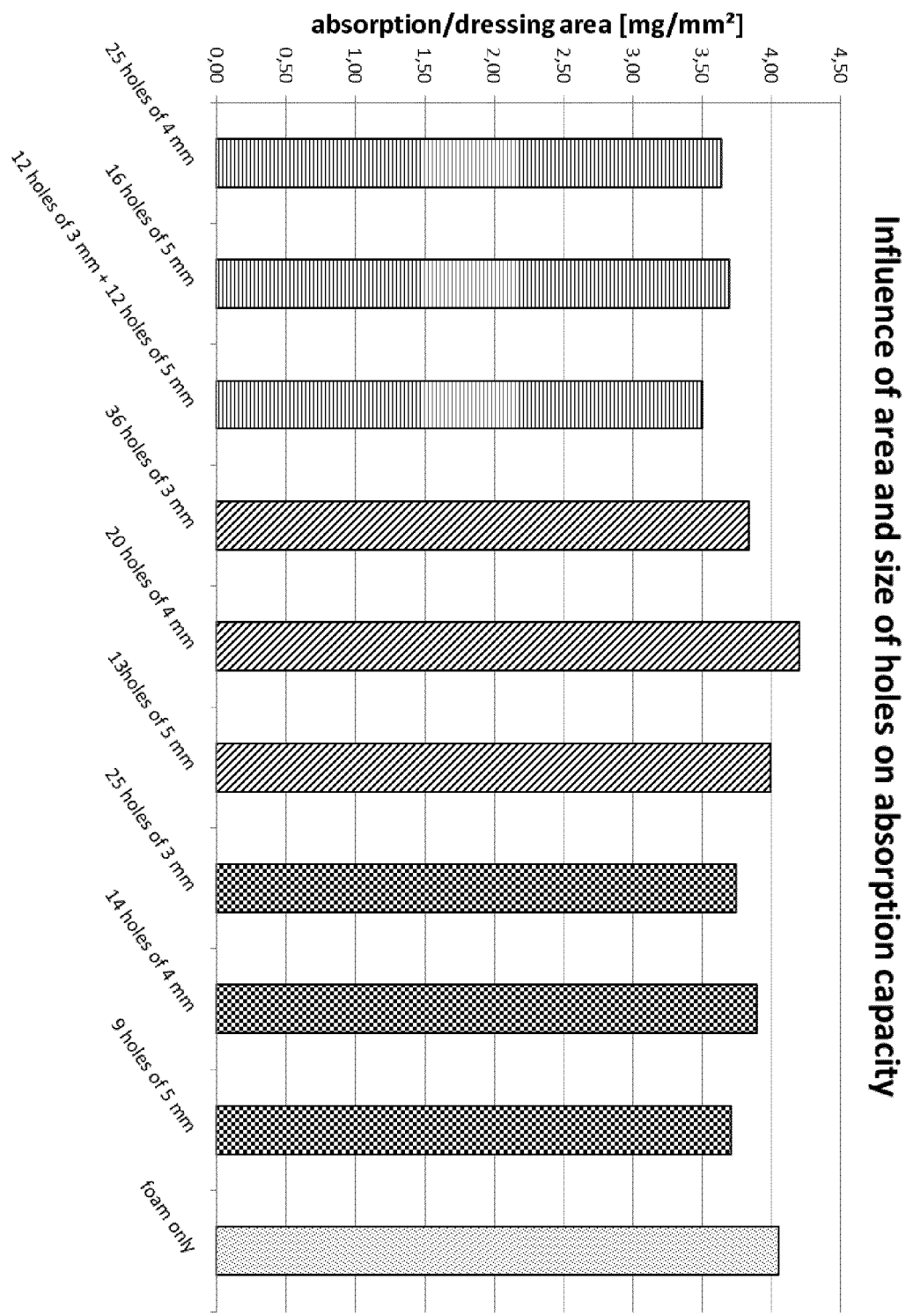
Figure 4:
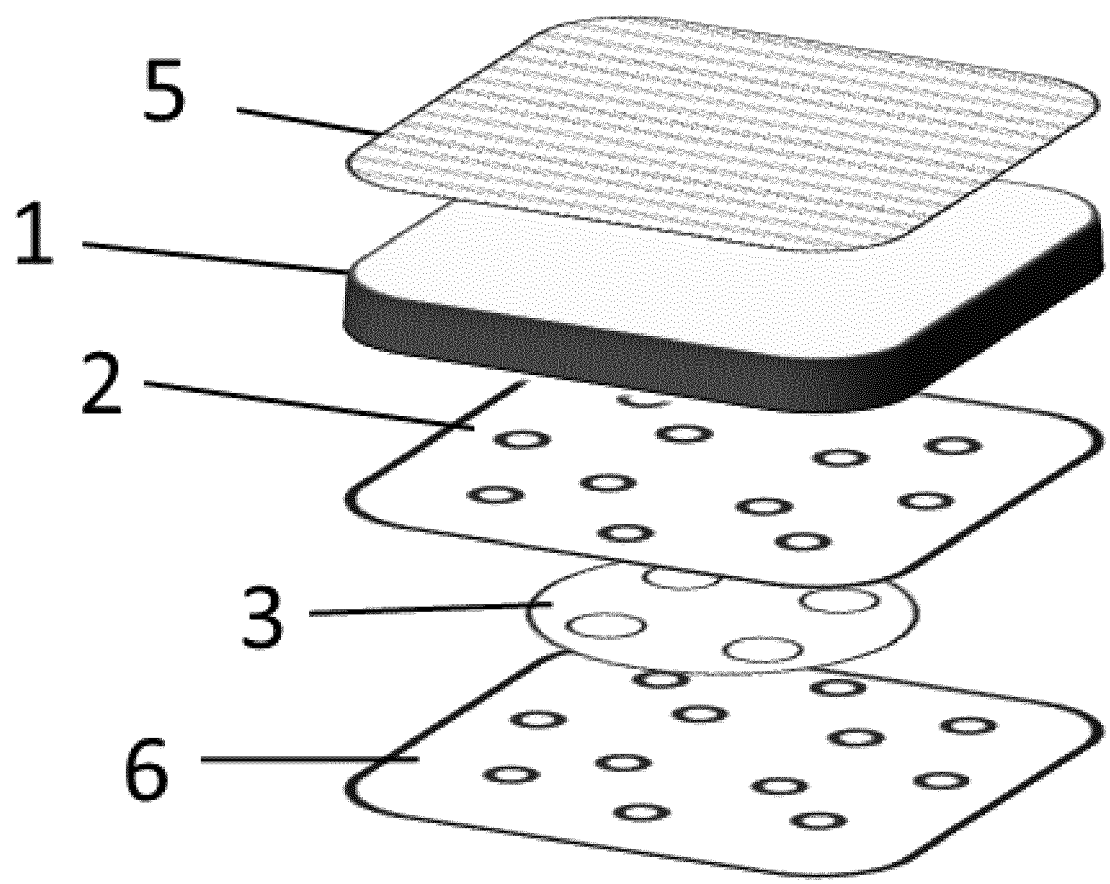

FIG. 3 shows the influence of the chosen perforation pattern on the absorption capacity of the wound care article FIG. 4 shows a principal sketch of the wound care product according to a further embodiment in a perspective view consisting of five layers, namely from top to bottom the cover layer 5, the liquid-absorbing layer 1, the occlusive layer 2, the active-agent releasing layer 3, and the gas-permeable layer 6 formed as a membrane. Note that the three most proximal layers comprise common circular perforations, so that the wound exudate can pass freely through these three layers in order to reach the liquid absorbing layer.

Figure 5:
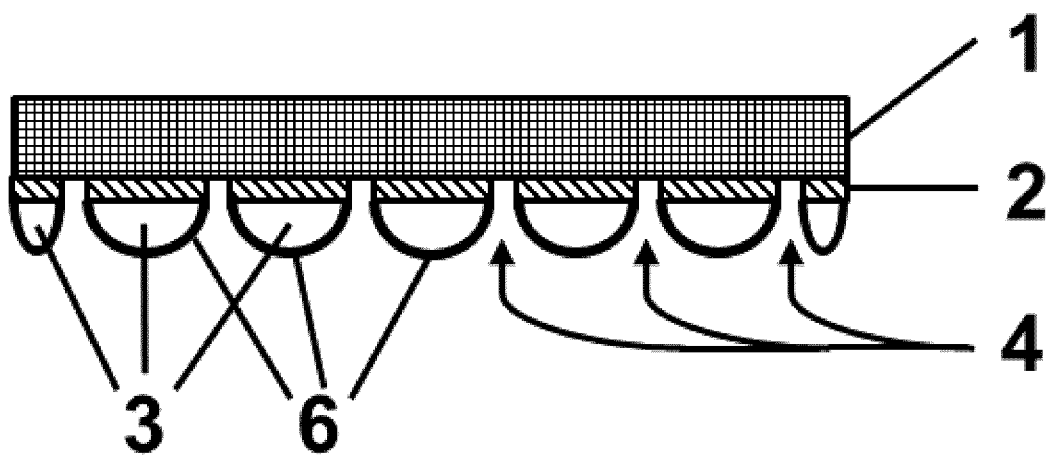

FIG. 5 shows a principal sketch of the wound care product according to another embodiment for release of a gas as active agent in cross section consisting of four layers, namely the gas-permeable layer 6, the gas releasing layer 3, the intermediate occlusive layer 2 and the liquid-absorbing layer 1 as top layer. Notably, the gas-permeable layer and the occlusive layer are sealed in the periphery and around the pores to surround the gas releasing layer, forming a pouch from which the gas can only be released through the gas-permeable layer facing the wound site.

While the invention has been illustrated and described in detail in the drawings and the foregoing description, such illustration and description are to be considered illustrative or exemplary and not restrictive.

From reading the present disclosure, other modifications will be apparent to persons skilled in the art. Such modifications may involve other features which are already known in the art and which may be used instead of or in addition to features already described herein.

Variations to the disclosed embodiments can be understood and effected by those skilled in the art, from a study of the drawings, the disclosure and the appended claims. In the claims, the word "comprising" does not exclude other elements or steps, and the indefinite article "a" or "an" does not exclude a plurality of elements or steps. The mere fact that certain measures are recited in mutually different dependent claims does not indicate that a combination of these measures cannot be used to advantage.

Any reference signs in the claims should not be construed as limiting the scope thereof.

LIST OF REFERENCE SIGNS 1 liquid absorbing layer
2 occlusive layer
3 active-agent releasing layer
4 pores
5 cover layer
6 Gas-release membrane as gas-permeable layer

The invention claimed is:

1. A multilayered wound care product comprising:
an upper liquid-absorbing layer;
an intermediate occlusive layer; and
a bottom active agent-releasing layer;
wherein the occlusive layer and the active agent-releasing layer are sheet-like layers with pores or perforations, wherein each pore or perforation is a common pore or perforation that extends through a whole thickness of both the intermediate occlusive layer and the active agent-releasing layer that enable a passage of wound exudate through the common pores or perforations of such two layers to reach the liquid-absorbing layer and simultaneously enable a release of an active agent from an area between the pores or perforations to enter a wound site, and
wherein the occlusive layer is impermeable for fluids and prevents the active agent from spreading to the upper liquid-absorbing layer.

2. The multilayered wound care product of claim 1, wherein the layers are connected by use of an adhesive or by welding, sealing or laminating using at least one of temperature and pressure.

3. The multilayered wound care product of claim 1, wherein the upper liquid-absorbing layer contains at least one absorbent material selected from a group consisting of polymer foams, sponges, hydrocolloids, hydrogels and hydrophilic polymers such as superabsorbing polymers.

4. The multilayered wound care product of claim 1, wherein the intermediate occlusive layer is a metal layer or a polymer layer of one of the following polymers: polyvinylidene chloride, polyethylene terephthalate (PET), oriented polypropylene (OPP), biaxially oriented polypropylene (BOPP), oriented polyamide (OPA), biaxially oriented polyamide (BOPA), or a multi-layer high barrier film, selected from a group consisting of polyethylene/ethyl vinyl alcohol copolymer/polyethylene (PE/EVOH/PE), PP/EVOH/PP, PP/EVOH/PE, polyamide/polyethylene (PA/PE), PE/PA/PE, PP/PA/PE, PA/EVOH/PA/PE and PP/PA/EVOH/PA/PE, EVOH/OPP, EVOH/BOPP, EVOH/OPA, EVOH/BOPA and PVDC/PET, or a metal-coated form of polymeric films.

5. The multilayered wound care product of to claim 1, wherein the active agent-releasing layer comprises an active agent being a therapeutic gas selected from a group consisting of oxygen, ozone, carbon dioxide, nitric oxide or combinations thereof, wherein the wound care product further comprises a gas-permeable layer oriented towards a treatment site having common pores or perforations with the active agent-releasing layer and the occlusive layer.

6. The multilayered wound care product of claim 1, wherein the active agent-releasing layer comprises different reactants that are separated from each other by a barrier, whereby breaking or removing the barrier allows a mixing of the reactants in order to generate the active agent.

7. The multilayered wound care product of claim 6, wherein a first reactant is an NO donor and a second reactant is a reducing agent or a proton donor.

8. The multilayered wound care product of claim 7, wherein the NO donor is selected from a group consisting of inorganic nitrite salts, alkyl nitrites, diazeniumdiolated organic compounds, trans[RuCl([15]aneN4)NO]$^{2+}$, Nitrosyl-ligands, 6-nitrobenzo[a]pyrol, S-nitroso-glutathione, S-nitroso-thiols, S-nitroso-N-acetyl-D-penicillamine (SNAP), L-arginine, L-citrulline, nitroglycerin (GTN), isosorbide 5-mononitrate (ISMN), isosorbide dinitrate (ISDN), pentaerythritol tetranitrate (PETN), erythrityl tetranitrate (ETN), amino acid derivatives, $N^6$-(Iiminoethyi) lysine) (L-NIL), L-$N^5$-(1-iminoethyi)ornithine (LN-NIO), $N^\alpha$-methyl-L-arginine (L-NMMA), S-nitroso glutathione (SNOG), S,S-dinitrosodithiol (SSDD), 2-[(pyridin-3-ylcarbonyl)amino]ethyl nitrate (nicorandil), sodium nitroprusside (SNP), S-nitroso-N-acetylpenicillamine (SNAP), [8-[2-hydroxy-3-(propan-2-ylamino)propoxy]-3,4-dihydro-2H-chromen-3-yl] nitrate (Nipradilol), 3-morpholino-sydnonimine (SIN-1), molsidomine, DEA-NONOate (2-(N,N-diethylamino)diazenolate-2-oxide), spermine NONOate (N-[4-[1-(3-aminopropyl)-2-hydroxy-2-nitrosohydrazino] butyl-1,3-propanediamine), 3-(5'-hydroxymethyl-2' furyl)-1-benzyl indazole (YC-1), nitroaniline derivatives, 2-methyl-2-nitrosopropane, imidazoyl derivatives, nitrate ester, hydroxyl nitrosamine, hydroxylamine and hydroxyl urea, and combinations thereof.

9. The multilayered wound care product of claim 8, wherein the inorganic nitrite salts are salt is selected from a group consisting of $LiNO_2$, $NaNO_2$, $KNO_2$, $RbNO_2$, $CsNO_2$, $FrNO_2$, $Be(NO_2)_2$, $Mg(NO_2)_2$, $Ca(NO_2)_2$, $Sr(NO_2)_2$, $Ba(NO_2)_2$, and $Ra(NO_2)_2$ and combinations thereof.

10. The multilayered wound care product of claim 7, wherein the reducing agent is selected from a group consisting of ascorbic acid, cysteine, glutathione, penicillamine, N-acetylcysteine, iodine, hydroquinone, mercaptosuccinic acid, thiosalicylic acid, methylthiosalicylic acid, dithiothreitol, dithioerythritol, 2-mercaptoethanol, $FeSO_4$, and $FeCl_2$, and combinations thereof.

11. The multilayered wound care product of claim 10, wherein the reducing agent is capable of forming a transient nitrosyl complex and is selected from a group consisting of Cu, Cu(I), V(III), Mo(VI), Fe(II), I⁻, Ti(III), Co(II), Mn(II), and Cr(III) and their salts.

12. The multilayered wound care product of claim 7, wherein the proton donor is selected from a group consisting of $H_2SO_4$, HCl, HBr, HI, $HNO_3$, acetic acid, lactic acid, tartaric acid, ascorbic acid, citric acid, salicylic acid, and combinations thereof.

13. The multilayered wound care product of claim 1, wherein the active agent-releasing layer is coated on a wound-facing side with an pressure sensitive adhesive wound contact layer, a material of which is selected from a group consisting of polyacrylate adhesive, silicone, natural rubber-based adhesive, synthetic rubber-based adhesive or hotmelt.

14. The multilayered wound care product of claim 1, wherein the pores or perforations have a triangular, rectangular, hexangular, ellipsoid or circular form.

15. The multilayered wound care product of claim 1, wherein the pores or perforations account for between 1% to 50%, of an area of at least one of the active agent-releasing layer and the occlusive layer.

16. The multilayered wound care product of claim 1, wherein the pores or perforations are evenly distributed on the area of the active agent releasing layer.

17. The multilayered wound care product of claim 1, wherein the occlusive layer exhibits a circumferential rim at the pores or perforation by projecting over an area of the active agent-releasing layer.

18. The multilayered wound care product of claim 1, wherein the upper liquid-absorbing layer, the intermediate occlusive layer, and the active agent-releasing bottom layer are bonded at a border portion or at edges of said layers.

19. A method of treatment of chronic wounds, comprising:
   providing the multilayered wound care product of claim 1; and
   applying the multilayered wound care product to treat one selected from a group consisting of: burns, partial and full-thickness wounds, pressure ulcers, venous ulcers, arterial ulcers, diabetic ulcers, chronic vascular ulcers, draining wounds, tunnelled or undermined wounds, surgical wounds, and trauma wounds.

* * * * *

UNITED STATES PATENT AND TRADEMARK OFFICE
CERTIFICATE OF CORRECTION

PATENT NO. : 10,500,300 B2
APPLICATION NO. : 16/471066
DATED : December 10, 2019
INVENTOR(S) : Verena Dybe et al.

Page 1 of 1

It is certified that error appears in the above-identified patent and that said Letters Patent is hereby corrected as shown below:

In the Specification

Column 3, Line 13, reads "product Specific embodiments are described below." and should read -- product. Specific embodiments are described below. --.

Column 13, Line 2, reads "membrane has a thickness between and 100 µm, thus rep-" and should read -- membrane has a thickness between 20 and 100 µm, thus rep- --.

In the Claims

At Claim 5, Column 28, Line 17, reads "5. The multilayered wound care product of to claim 1," and should read -- 5. The multilayered wound care product of claim 1 --.

At Claim 9, Column 28, Line 59, reads "wherein the inorganic nitrite salts are salt is selected from a" and should read -- wherein the inorganic nitrite salts are selected from a --.

Signed and Sealed this
Third Day of March, 2020

Andrei Iancu
*Director of the United States Patent and Trademark Office*